United States Patent
Hatch et al.

(10) Patent No.: US 11,789,510 B2
(45) Date of Patent: Oct. 17, 2023

(54) DATA AND POWER ADAPTER FOR HOSPITAL ASSISTANCE CALLS

(71) Applicant: Hatchmed Corporation, Seattle, WA (US)

(72) Inventors: Brian Hatch, Seattle, WA (US); Kyrylo Keydanskyy, Seattle, WA (US)

(73) Assignee: HATCHMED CORPORATION, Seattle, WA (US)

( * ) Notice: Subject to any disclaimer, the term of this patent is extended or adjusted under 35 U.S.C. 154(b) by 0 days.

(21) Appl. No.: 17/004,914

(22) Filed: Aug. 27, 2020

(65) Prior Publication Data

US 2022/0066525 A1 Mar. 3, 2022

(51) Int. Cl.
| | |
|---|---|
| G06F 1/26 | (2006.01) |
| G06F 13/10 | (2006.01) |
| G16H 40/63 | (2018.01) |
| H04B 1/3827 | (2015.01) |

(52) U.S. Cl.
CPC ............ *G06F 1/266* (2013.01); *G06F 13/102* (2013.01); *G16H 40/63* (2018.01); *H04B 1/3827* (2013.01)

(58) Field of Classification Search
CPC ....... G06F 1/266; G06F 13/102; G16H 40/63; H04B 1/3827
See application file for complete search history.

(56) References Cited

U.S. PATENT DOCUMENTS

| | | | |
|---|---|---|---|
| 9,147,965 B2 | 9/2015 | Lee | |
| 2002/0140675 A1* | 10/2002 | Ali | A61B 5/14551 345/158 |
| 2006/0058587 A1* | 3/2006 | Heimbrock | A61G 7/05 600/300 |
| 2016/0008197 A1* | 1/2016 | Zerhusen | A61G 7/0513 5/503.1 |
| 2016/0140827 A1* | 5/2016 | Derenne | A61B 5/747 340/573.7 |
| 2017/0221344 A1* | 8/2017 | Cox | G16H 40/67 |
| 2018/0293849 A1* | 10/2018 | Bhimavarapu | A61B 5/7475 |
| 2018/0317826 A1* | 11/2018 | Muhsin | G16H 40/63 |
| 2020/0113488 A1* | 4/2020 | Al-Ali | A61B 5/744 |
| 2020/0327784 A1 | 10/2020 | Bodurka et al. | |

* cited by examiner

*Primary Examiner* — Nimesh G Patel
(74) *Attorney, Agent, or Firm* — Kilpatrick Townsend & Stockton LLP

(57) ABSTRACT

A data and power adapter (DPA) for assistance requests is described. The DPA includes multiple interfaces. A first interface communicatively couples a backend computer and a patient device of a health care facility. Services to and from the patient device can be supported through the first interface. A second interface communicatively couples a personal electronic device (PED) and/or a PED holder and the backend computer and provides power from a power source of the health care facility to the PED and/or PED holder. The PED may include an assistance request button. In this way, some or all of the services, including assistance request services, can also be supported via the PED and/or PED holder.

22 Claims, 8 Drawing Sheets

US 11,789,510 B2

DATA AND POWER ADAPTER FOR HOSPITAL ASSISTANCE CALLS

BACKGROUND

Portable electronic devices (PEDs) (e.g., digital tablets, smart phones, and other electronic devices) are becoming more popular and prevalent in modern day lifestyles. Hospitals are experiencing increased usage of PEDs, either by patients and/or by hospital personnel. PEDs are being used in hospitals for communication, education, video conferencing with a patient who is in a hospital bed, and entertainment of the patient.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments herein are directed to a data and power adapter for hospital assistance calls, the data and power adapter comprising: a housing; a first connector in the housing, the first connector comprising first connections with a nurse call system of a hospital; and a second connector in the housing, the second connector comprising a first set of connections for power to a personal electronic device (PED), the second connector further comprising a second set of connections for an assistance request signal from an assistance request button to the nurse call system; and a third connector in the housing, the third connector comprising third connections with a patient bed system of the hospital, wherein a subset of the first connections of the first connector and the second set of connections of the second connector are coupled. Embodiments herein are also directed to a system for hospital assistance calls, the system comprising: a data and power adapter that comprises: a housing; a first set of connectors disposed in the housing, the first set of connectors configured to connect the data and power adapter with a nurse call system of a hospital and with a patient bed system of the hospital; and a power and data cable comprising a second set of connectors, the second set of connectors configured to connect the power and data cable with the data and power adapter, with the patient bed system, and with a personal electronic device (PED).

For a fuller understanding of the nature and advantages of the present invention, reference should be made to the ensuing detailed description and accompanying drawings.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
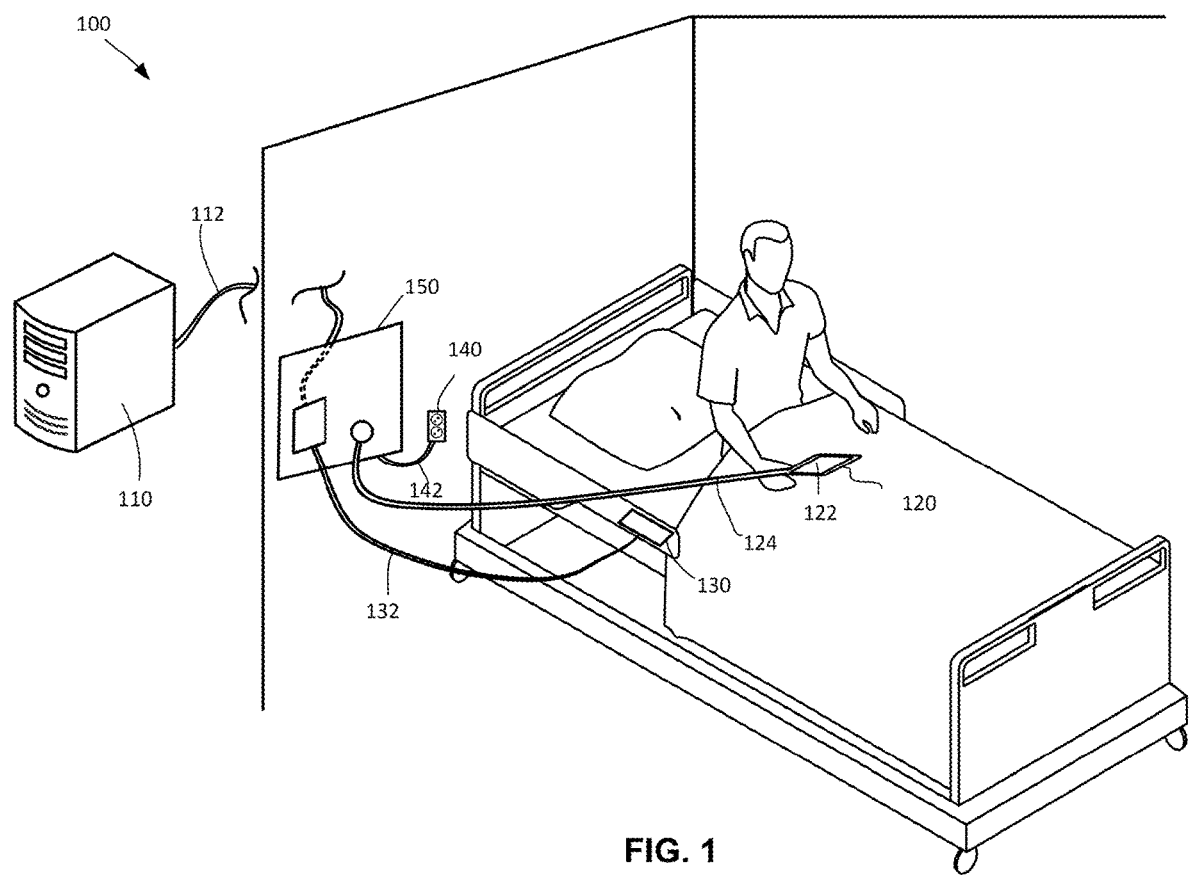
FIG. 1 illustrates a system for hospital assistance calls, in accordance with embodiments of the present disclosure.

In the following description, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

With the increase in use of PEDs in health care facilities, such as hospitals, providing data and power to the PEDs from systems of the health care facilities becomes advantageous. In an example, a health care facility includes a system that provides services to a patient. For instance, the system can include a backend computer, a health care provider device, and a patient device (e.g., a hospital pillow speaker). The patient device allows the patient to request assistance by generating and sending an assistance request signal to the backend computer. In turn, the backend computer may send a notification to the health care provide device about the assistance request. In such a system, it can be advantageous to also communicatively couple the PED of the patient (or one provided by the health care facility to the patient) with the backend computer and to provide power to the PED. In this way, the patient's PED can be powered, as needed, throughout the visit and the PED is usable to generate and send the assistance request to the backend computer. As used herein, a PED refers to an electronic device that can support a personal use, where the user of the PED may but need not be the owner of the PED.

To do so, embodiments of the present disclosure involve a data and power adapter (DPA) for assistance requests. The DPA includes multiple interfaces. A first interface communicatively couples the backend computer and the patient device. In this way, the services to and from the patient device can still be supported. A second interface communicatively couples the PED and/or a holder of the PED (referred to herein as a PED holder) and the backend computer and provides power from a power source of the health care facility to the PED and/or PED holder. The PED may include an assistance request button. For instance, this button may be implemented as part of a software application stored and expected by the PED, where the application presents the assistance request button as a soft button on a graphical user interface. Similarly, the PED holder can include an assistance request button. In this way, some or all of the services, including assistance request services, can also be supported via the PED and/or PED holder.

In addition, the DPA may include status indicators related to the power and the services. For instance, the status indicators can be implemented as light sources. A first light source can visibly indicate the state of the power to the PED and/or PED holder. A second light source can visibly indicate the connection state of the PED and/or PED holder. And a third light source can visibly indicate the connection state of the patient device.

Generally, the DPA can supervise, at least electrically, whether an assistance request can be placed from the assistance request button or not. Electrical supervision is defined as using a circuit to detect whether the assistance request button is operable when a user (e.g., a patient) needs to place an assistance request. Many reasons exist for inoperability including any of: (1) and open circuit, (2) a severance of a cable (e.g. a bed cable connected to the PED through the PED holder), or (3) a short circuity. The open circuit can occur when the cable becomes unplugged rendering the assistance request button unusable. This happens most often when the cable is tied to a rail of a bed (e.g., a hospital bed), and then the bed is moved (to move patient or simply by housekeeping to clean the area). The severance can occur when the cable itself is damaged (e.g., cut, disconnected, etc.) rendering the assistance request button unusable. This happens most commonly when the cable is run over or caught in a bed caster. The short circuit can occur when the cable becomes damaged and the conductors used for the assistance request function are shorted, so that the assistance request button is rendered unusable. This happens most commonly when the cable is run over and caught in a bed caster, the short created by pinching the caster into wires of the cable.

One method of electrical supervision relies on a resistor ladder. There is a resistor value connected to one conductor of the cable to the positive voltage rail. There is a second resistor value connected to the other conductor of the cable to the negative voltage rail. There is a third resistor placed in parallel with an assistance request switch. Each conductor can have a voltage in this idle state. If the cable is severed, or the cable is shorted, or the assistance request button is pressed, those voltages change. The change is detected and the detection is used to create an assistance request. In the case of an actual assistance request, the duration of the voltage change is typically short, corresponding to the time the user would press the button. This signal is passed to the nurse call system and initiates a normal assistance request. This assistance request can be reset remotely by a staff member answering the assistance request at a console or a mobile device or by resetting at the bedside. If a fault (open or short) occurs, the voltage change is steady state. The assistance request is continuously placed and can only be reset by going to the room and correcting the issue. This assistance request would essentially be instantaneous with the fault occurrence, and well within the UL1069 requirement of ninety seconds for a supervisory alarm to be initiated.

A second method of supervision includes using a microprocessor at the switch location and another microprocessor at the wall location. The microprocessor on the wall side can be set up to send periodic messages over the cable. The microprocessor at the assistance request button side would acknowledge the transmission and send a reply. If the cable was disconnected, shorted or severed, the wall side microprocessor would then initiate the un-resettable assistance request into the nurse assistance request system. UL1069 sets a requirement for supervision to react within ninety seconds of a fault event.

In an example, the DPA operates in a supervised normally open circuit mode (e.g., a mode that relies on electrical supervision of an open circuit). In other words, the DPA includes electrical circuitry that creates, under normal operations, an open circuit at the interface to the nurse call system. Upon an assistance request signal from the assistance request button of the PED and/or PED holder, the electric circuitry creates a short circuit at the interface. Upon a data disconnect between the DPA and the PED and/or PED holder, the electric circuitry also creates a short circuit at the interface. The nurse call system can detect the assistance request and the disconnection based on the short circuits and send the relevant notifications to the health care provider device.

In the interest of clarity of explanation, various embodiments of the present disclosure are described in connection with a supervised normally open circuit mode. However, the embodiments are not limited as such. As explained herein above, the embodiments can rely on electrical supervision. This supervision can be for any of open circuit, cable severance, and/or short circuit.

In also the interest of clarity of explanation, various embodiments of the present disclosure are described in connection with a hospital, assistance request button, and a PED holder. However, the embodiments are not limited as such. For example, the embodiments similarly apply to any type of a health care facility and any type of services provided to a patient via the PED or attachments to the PED. These services can be implemented partially or fully as an application installed on the PED and/or as application(s) and/or hardware installed on the attachments connected to the PED. For instance, the assistance request button can be implemented as a soft button on the PED, a hard button on the PED holder, and/or a hard button on a cable that connects the PED holder to the DPA. In another illustration, the services can include providing controls to a bed and/or a television of the health care facility. One or more soft buttons on the PED, one or more hard buttons on the PED holder, and/or one or more hard buttons on the cable may be implemented, where the DPA may couple such button(s) with the relevant patient bed system(s) (e.g., with the bed or the television).

FIG. 1 illustrates a system 100 for hospital assistance calls, in accordance with embodiments of the present disclosure. The system 100 includes a nurse call system 110, a PED holder 120, a bed connector 130, a power outlet 140, and a DPA 150. The DPA 150 communicatively couples the nurse call system 110 with the bed connector 130 through a first interface and the nurse call system 110 with the PED holder 120 through a second interface. The DPA 150 also supplies power from the power outlet 140 to the PED holder 120. The DPA 150 can have an in-wall installation or an on-wall installation relative to a wall (e.g., a wall in a patient room). Wire routing to and from the DPA 150 can be to the back and/or face of the DPA 150 depending on the installation type.

In an example, the nurse call system 110 is implemented as a backend computer that provides various services to patient devices of the hospital. These services include, for instance, supporting nurse assistance calls from and to such patient devices. A patient device can include an end system connected to the bed connector 140, such as a pillow speaker.

The PED holder 120 includes an assembly of mechanical and electrical components to hold the PED 122, provide power to the PED 122, and provide a data connection between the nurse call system 110 and the PED 122 and/or an assistance request button on the PED holder 120. An example of the PED holder 120 is disclosed in U.S. patent application Ser. No. 16/035,283 filed on Jul. 13, 2018, titled "Portable Electronic Device Holder With Assistance Request Button And Method Powering Portable Electronic Device," which is incorporated herein in its entirety by reference. The PED 122 can be any suitable portable electronic device, for example, a mobile phone, a smart phone, a personal digital assistant (PDA), a laptop computer, a desktop computer, a thin-client device, a tablet PC, an electronic book (e-book) reader, or other computing devices or electronic devices.

The bed connector 130 represents an electrical and/or magnetic connector that can be mounted to a bed of the hospital and that can connect one or more patient bed systems to the nurse call system 110 and/or other systems of the hospital through the DPA 150. An example of the bed connector 130 is disclosed in U.S. Pat. No. 9,147,965 granted on Sep. 29, 2015, titled "Magnetic-enabled connector device," which is incorporated herein in its entirety by reference. A patient bed system represents a system available on the bed or nearby to the bed and usable to access certain services, such as controlling the bed, making a nurse call request, controlling a television, and the like. Each of a pillow speaker, a smart bed, a bed with power and/or data connections, a bed management unit that can collect data of a patient using the bed, and any combination thereof is an example of a patient bed system.

The power outlet 140 may be available from a wall of a hospital room or may be mounted on the bed or some other fixture in the hospital room. The power outlet 140 generally supplies power from a power source of the hospital. The power can be provided at a 110 VAC, 220 VAC, 12 VDC, 5 VDC, or at some other voltage range.

As illustrated, the nurse call system 110 is coupled with the DPA 150 via a set of cables 112. This coupling can be direct or can be through a set of connectors (e.g., a wall connector mounted on a wall of the hospital room). Further, a wireless connection may be additionally or alternatively used depending on the capabilities of the nurse call system 110. If a cable is used, the DPA 150 includes a wired interface, such as an electrical connector, to which the cable can be connected. If a wireless connection is used, the DPA 150 includes a wireless interface to the nurse call system 110, such as a wireless network interface.

The PED holder 120 is coupled with the DPA 150 via a set of cables 124. A cable in this set 124 can be a multifunctional cable in the sense that it includes electrical wires dedicated to providing electrical power and electrical wires dedicated to providing data signals. The multifunctional cable can include a connection to an assistance request button or can integrate such a button. A wireless connection may be additionally or alternatively used between the PED holder 120 and the DPA 150. In such a case, the DPA 150 includes a wireless interface (e.g., a same or a different wireless network interface card as above). The wireless interface may be used for exchanging the data signals, whereas the set of cables 124 may be used for providing power (and, optionally, for data signal exchange) or may be eliminated.

The bed connector 130 is coupled with the DPA 150 via a set of cables 132. A cable in this set 132 can include a set of electrical wires to provide data signals to and from a patient bed system connected with the bed connector 130. The DPA 150 couples the patient bed system with the nurse call system 110. This coupling can include connecting the set of cables 132 with the set of cables 112. Additionally or alternatively, if a wireless connection is used, the coupling can include connecting the set of cables 132 with the network interface card of the DPA 150 to the nurse call system 110. Here also, a wireless connection may be additionally or alternatively used between the bed connector 130 and the DPA 150, in which case the DPA 150 includes a wireless interface (e.g., a same or a different wireless network interface card as above). As further illustrated in FIG. 10, the set of cables 124 and the set of cables 132 may be integrated in a single cable having a portion going to the PED 122, a portion going to the bed connector 130, and a portion going to the DPA 150.

The power outlet 140 is coupled with the DPA 150 via a set of cables 142. Depending on the type of the power source, the coupling can also include a power converter. For instance, if the power outlet 140 supplies 110 VAC or 220 VAC, an AC to DC power converter (e.g., from 110 VAC or 220 VAC to 12 VDC or 5 VDC) can connect the power outlet 140 to the DPA 150 via the set of cables 142. Alternatively, the DPA 150 may include this power converter.

Figure 2:
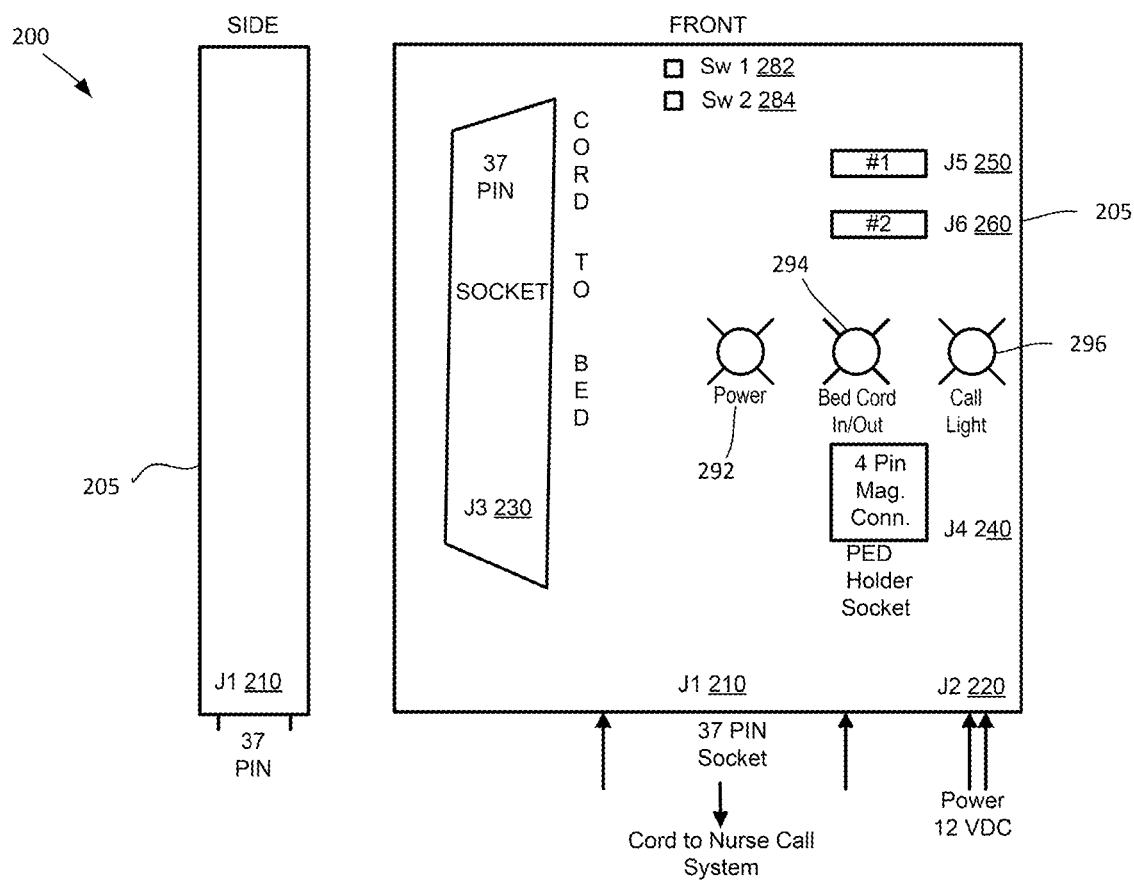
FIG. 2 illustrates a data and power adapter for hospital assistance calls, in accordance with embodiments of the present disclosure.

FIG. 2 illustrates a DPA 200 for hospital assistance calls, in accordance with embodiments of the present disclosure. A side view of the DPA 200 is shown on the left side of FIG. 2. A front view of the DPA 200 is shown on the right side of FIG. 2. As illustrated, the DPA 200 includes a housing 205 made out of rigid material, such as plastic or metal, and shaped in a particular configuration, such as a rectangular box. The housing 205 includes cutouts, where different hardware components of the DPA 200 are installed. These electrical components include a set of electrical connectors and/or magnetic connectors, a set of switches, and a set of lights.

In an example, a nurse call system connector 210 (e.g., a first connector) is installed in the housing 205. This connector 210 can be an electrical connector, a magnetic connector, and/or a fiber connector that that can be coupled, via one or more wired connections, with a nurse call system, such as the nurse call 110 of FIG. 1. Additionally or alternatively, the connector 210 can be a radio frequency connector and/or an optical connector that can be coupled, via one or more wireless connections, with the nurse call system. For instance, the nurse call system connector 210 is a multiple pin connector at the bottom, center of the housing 205, such as a thirty-seven pin female connector. In another illustration, the nurse call system connector 210 is a power-over-Ethernet (POE) connector.

A power input connector 220 (e.g., a second connector) is also installed in the housing 205. The power input connector 220 can be an electrical connector that can be coupled with a power outlet, such as the power outlet 140 of FIG. 1. For instance, the power input connector 220 is a multiple pin connector at the bottom right of the housing 205, such as a two-pin female connector. Additionally or alternatively, the DPA 200 can include a local power source, such as a set of batteries. In this case, the power input connector 220 may, but need not, be omitted.

A hospital bed connector 230 (e.g., a third connector) is also installed in the housing 205. The hospital bed connector 230 can be an electrical connector, a magnetic connector, and/or a fiber connector that can be coupled, via one or more wired connections, with a bed connector, such as the bed connector 130 of FIG. 1. Additionally or alternatively, the hospital bed connector 230 can be a radio frequency connector and/or an optical connector that can be coupled, via one or more wireless connections, with the bed connector 130. For instance, the hospital bed connector 230 is a multiple pin connector at the front left of the housing 205, such as a thirty-seven pin female connector.

In the example of a thirty-seven pin female connector, some of the pins in the hospital bed connector 230 can carry one or more signals. The signals include, for instance, a bed awareness status on pin "1," a read light on pin "2," a rom light on pin "3," a speaker high on pin "4," a potentiometer wiper on pin "5," a bed exit status on pin "6," a nurse call interlock on pin "7," a negative audio transfer on pin "8," a positive audio transfer on pin "9," a positive interlock on pin "10," a negative interlock on pin "11," a bed awareness alert on pin "12," no connection on pin "13" (e.g., pin "13" may not carry a signal), a potentiometer low common on pin "14," a potentiometer high common/audio STV on pin "15," a positive answer light on pin "16," a bed awareness alert on pin "17," a bed awareness side rail alert on pin "18," a positive nurse call light on pin "19," no connection on pins "20," "21," and "22" (e.g., each of these pins may not carry a signal), a brake status "on" on pin "2," no connection on pin "24" (e.g., pin "24" may not carry a signal), a positive nurse call on pin "25," a nurse call NO/NC on pin "26," a room/read light common on pin "27," a negative nurse call light on pin "28," a negative nurse answer light on pin "29," a priority NO/NC on pin "30," a priority common on pin "31," a bed awareness low height alert on pin "32," a negative TV/Data (STV) on pin "33," a positive TV/Data (STV) on pin "35," a speak low common on pin "35," an audio shield on pin "36," and a bed awareness common pin "37."

A PED connector 240 (e.g., a fourth connector) is also installed in the housing 205. The PED connector 240 can be an electrical connector a magnetic connector, and/or a fiber connector that can be coupled, via one or more wired connections, with a PED or a PED holder, such as the PED holder 120 of FIG. 1. Additionally or alternatively, the PED connector 240 can be a radio frequency connector and/or an optical connector that can be coupled, via one or more wireless connections, with the PED or the PED holder. For instance, the PED connector 240 is a multiple pin connector at the bottom front, right of the housing 205, such as four pin magnetic connector or a four pin female connector.

Multiple USB connectors, such as a first USB connector 250 (e.g., a fifth electrical connector) and a second USB connector 260 (e.g., a sixth electrical connector) are also installed in the housing 205. Each USB connector can be a type A, B, mini-USB, or micro-USB female socket connector that can be coupled with a PED, such as the PED holder 122 of FIG. 1. For instance, each USB connector includes four pins or nine pins according to the USB 2.0 or 3.0 standard and is installed near the top front, right of the housing 250.

Additionally, multiple electrical switches, such as a first electrical switch 282 and a second electrical switch 284 are also installed in the housing 205, such as near the top front, center of the housing 205. These switches can be used to control some of the services of the DPA 120. For instance, the first electrical switch 282 can disengage certain pins of the nurse call system connector 210 and/or the hospital bed connector 230 to prevent a data signal from being generated in case the hospital wishes to disconnect a bed (e.g., decouple the bed connector 130), where this data signal would have indicated the disconnection. Similarly, the second electrical switch 284 can disengage certain pins of the PED connector 240 to prevent a data signal from being generated in case the hospital wishes to disconnect a PED holder, where this data signal would have indicated the disconnection. In this way, the electrical switches 282 and 284 can replace dummy plugs in order to prevent cord out alarms for disconnections.

Furthermore, multiple indicators of operational modes of the DPA 200 are also installed in the housing 205, such as near the center front, right of the housing 205. The indicators can includes light sources that provide visible indications of the operations. A first light source 292 can indicate whether power is available to a PED through the PED connector 240 and/or the USB connectors 250 and 260. A second light source 294 can indicate whether a bed is disconnected (e.g., whether the bed connector 130 is decoupled). A third light source 296 can indicate whether an assistance request to the nurse call system can be initiated from an assistance request button on a PED holder of the PED, the PED itself, and/or a cable coupling the PED holder or PED with the DPA 200.

In an example, the operational modes of the DPA 200 are implemented such that its idle operational (or normal operation) mode is a supervised normally open circuit mode. In this example, the operational modes that can be detected and used include the idle mode, a disconnected mode, and an assistance request mode. These modes can be detected based on voltage measurements by a voltage monitoring circuit of the DPA 200 as further described in connection with the next figures. The idle mode indicates that the assistance request button is electrically coupled to the PED connector 240 and that no assistance request signal exists on a set of electrical connections of the PED connector 240. In the idle mode, an assistance request can be initiated from the assistance request button. The disconnected mode indicates that the assistance request button is electrically disconnected from the PED connector 240, and thus, no assistance request can be initiated from the assistance request button. The assistance request mode indicates that the assistance request signal exists on the set of electrical connections of the PED connector 240. In other words, the assistance request mode is entered upon an initiation of an assistance request from the assistance request button.

In this example, an emission property of at least the third light source 296 varies between the multiple operational modes of the DPA 200. The emission property includes at least one of a wavelength of emitted light, an intensity of the emitted light, or an emission pattern of the emitted light. For instance, the third light source 296 can be controlled to emit a green light when the DPA 200 is in idle mode, emit a red light (or may be turned off, or flash according to a pattern) when the DPA 200 is in the disconnected mode, and emit a blue light when the DPA 200 is in the assistance request mode.

Although not illustrated in FIG. 2, the DPA 200 can include additional or alternative components. For instance, the DPA 200 can include an illumination source that projects light to the wall where the DPA 200 is installed, to the floor, to the ceiling, and/or to the bed. the light projections can be controlled to indicate information received from a nurse call system and/or a PED. Similarly, the DPA 200 can include a proximity sensor. Operations of the DPA 200 can be activated (e.g., power and/or data can become available) upon detection of a proximity of a person (e.g., patient or physician) by the proximity sensor, and deactivated otherwise.

Figure 3:
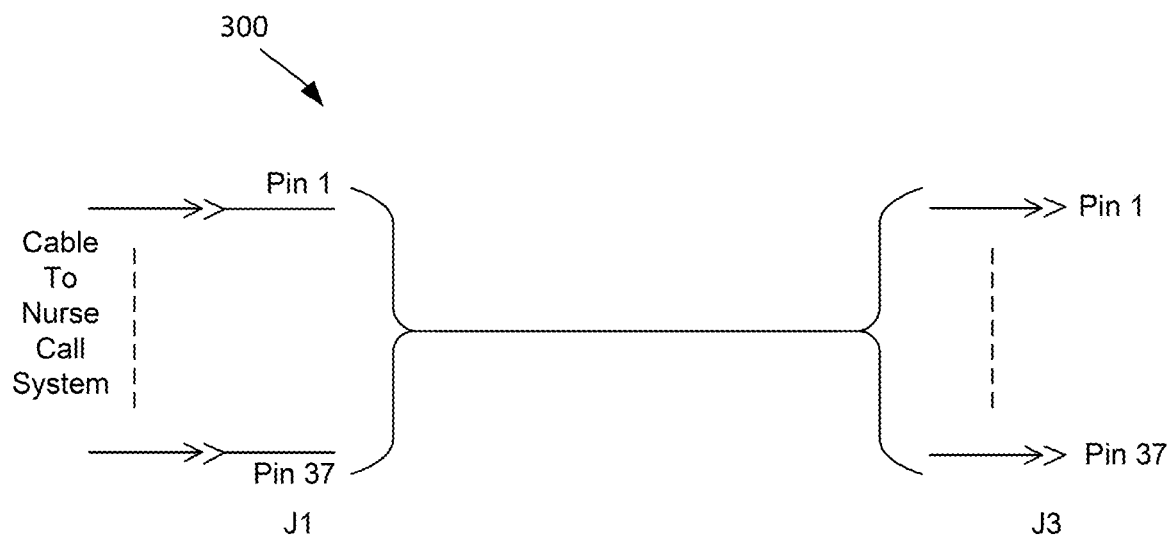
FIG. 3 illustrates example connections between a nurse call system connector and a hospital bed connector, in accordance with embodiments of the present disclosure.

FIG. 3 illustrates example connections 300 between a nurse call system connector and a hospital bed connector, in accordance with embodiments of the present disclosure. The nurse call system connector and the hospital bed connector are examples of the nurse call system connector 210 and the hospital bed connector 230 of FIG. 2, respectively.

In an example, the nurse call system connector includes first electrical connections, such as first pins, that can be connected to a nurse call system of a hospital. In comparison, the hospital bed connector includes second electrical connections, such as second pins, that can be connected to a patient bed system on a bed of the hospital. The connections 300 include a set of electrical wires that connects the first electrical connections with the second electrical connections. As illustrated, the connections 300 can be one-to-one connections between the pins. For instance, each of the nurse call system connector and hospital bed connector is a thirty seven pin connector. Each pin from each connector is connected only to an equivalent pin of the other connector.

Figure 4:
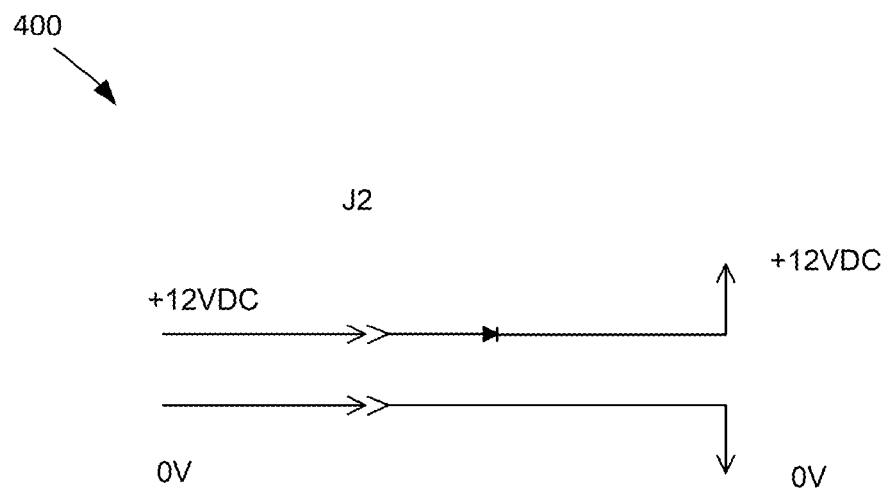
FIG. 4 illustrates an example pinout of a power input connector, in accordance with embodiments of the present disclosure.

FIG. 4 illustrates an example pinout 400 of a power input connector, in accordance with embodiments of the present disclosure. Power from a power source of a hospital can be supplied to the power input connector via a power outlet, such as the power outlet 140 of FIG. 1. The power input connector is an example of the power input connector 220 of FIG. 2.

In an example, the supplied power is a 12 VDC power. A voltage converter may be installed between the power outlet and the power input connector. In this example, the power input connector includes electrical connections that can be connected to the power source via the voltage converter and power outlet. These electrical connections can include electrical pins and one or more Zener diodes. For instance, the power input connector is a two-pin female connector with a first pin connected to the 0 VDC line and a second pin connected to the 12 VDC line and Zener diode.

Of course other configurations are possible depending on the supplied power. For instance, AC power may be supplied to the DPA and the power input connector can supply this power to an AC to DC converter in the DPA.

Figure 5:
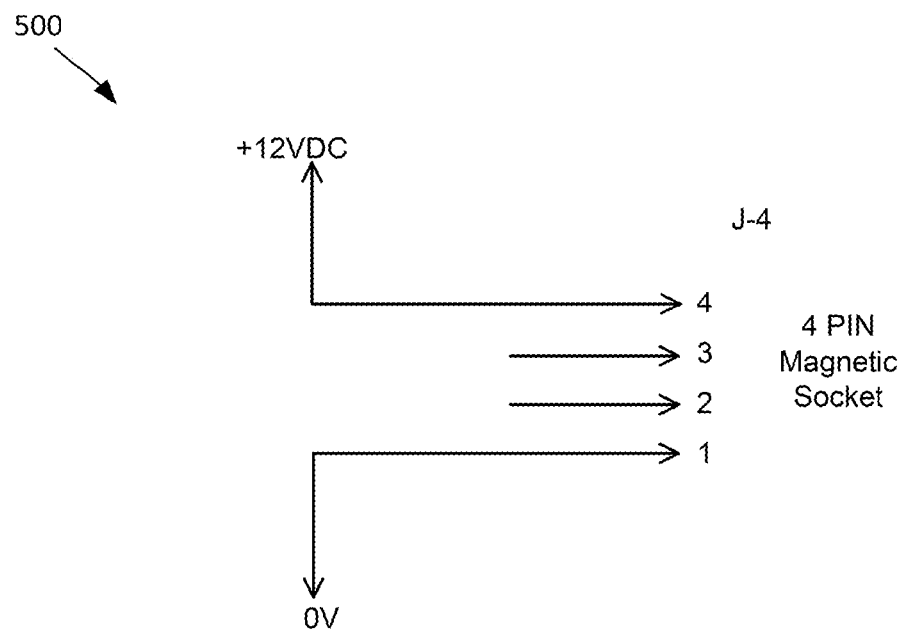
FIG. 5 illustrates an example pinout of a personal electronic device (PED) connector, in accordance with embodiments of the present disclosure.

FIG. 5 illustrates an example pinout 500 of a PED connector, in accordance with embodiments of the present disclosure. The PED connector is an example of the PED connector 240 of FIG. 2, and can be connected to a power input connector to receive power, to a PED holder to supply the power and exchange data signals, and to a nurse call system connector and/or a hospital bed connector, to exchange the data signals. Hence, the PED connector includes multiple sets of electrical connections, such as pins. A first set of electrical connections are for the power. A second set of electrical connections are for assistance request signals from an assistance request button to a nurse call system, where the assistance request button is on the PED holder, a PED in the PED holder, and/or a cable between the PED holder or the PED and the DPA.

As illustrated, the PED connector is a four pin connector. A first pin is connected to a 12 VDC line from the power input connector. A second pin is connected to the 0 VDC line from the power input connector. These two pins are coupled (e.g., via a first set of wires) with pins of the power input connector and can be referred to herein as power pins. A third pin and fourth pin are used for the data signals (e.g., the assistance request signals). These pins are coupled (e.g., via a second set of wires) to pins of the nurse call system connector (or to the equivalent pins of the hospital bed connector) as further described in connection with the next figures. Accordingly, a multifunctional cable can be plugged into the PED connector to couple the first two pins with a power pins of a connector on the PED holder and to couple the last two pins with data pins of the connector on the PED holder.

In the illustrative example of FIG. 5, the third and fourth pins (e.g., referred to herein as data pins) can pass voltage within a certain range corresponding to an assistance request signal. The assistance request signal (or the corresponding voltage across the two pins) represents data for an assistance request (referred to herein as assistance request data). Other types of data can be supported via the two data pins. For instance, if control data for controlling a hospital bed should be supported, corresponding control signals can be multiplexed over the two data pins. In another illustration, data connectivity between a USB connector of the DPA and the PED connector may be desired (in this way, a patient can plug a first PED in the PED connector and a second PED in the USB connector and transfer data between the two PEDs). In this case, the data connectivity can be supported by also multiplexing the corresponding signals over the two data pins. In yet another illustration, the DPA can include a network interface card to receive connectivity data from a network (e.g., the connectivity data here can represent data downloads and/or uploads from a web site via the Internet). Also in this case, the data connectivity can be supported by multiplexing the corresponding signals over the two data pins. Additionally or alternatively, the PED connector can include further data pins dedicated to the other type(s) of data (e.g., control data, connectivity data, etc.).

Figure 6:
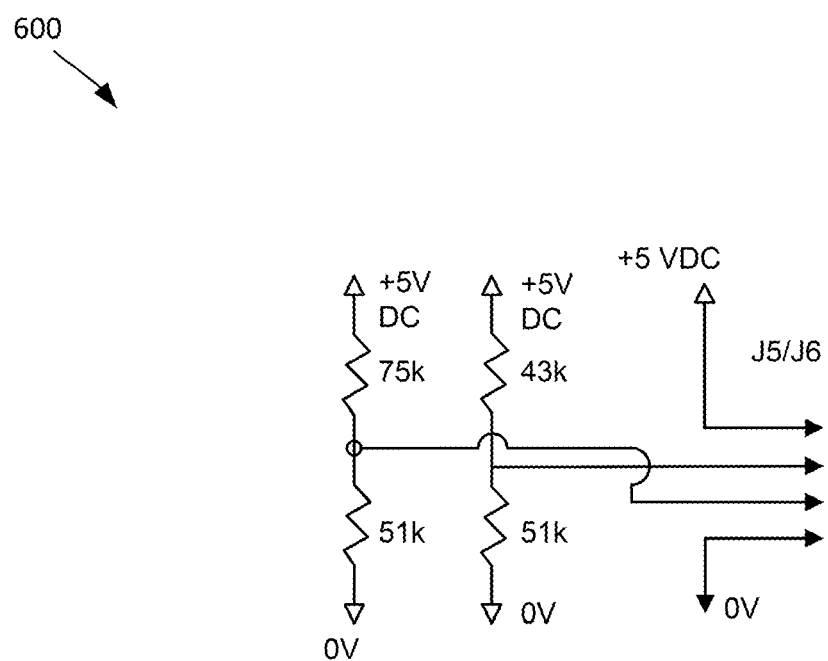
FIG. 6 illustrates an example pinout of a universal serial bus (USB) connector, in accordance with embodiments of the present disclosure.

FIG. 6 illustrates an example pinout 600 of a USB connector, in accordance with embodiments of the present disclosure. The USB connector is an example of the USB connector 250 or 260 of FIG. 2.

In an example, the USB connector includes multiple pins. Two of the pins are connected to power and two other pins are connected to a control network. The power may be supplied from a power converter of the DPA, such as from a 12 VDC to a 5 VDC converter. Power to the converter can be supplied from a power input connector, such as the power input connector 230 of FIG. 2. The control network can control the voltage output to the other two pins. This voltage output indicates to a PED plugged into the USB connector whether fast charging is available or not. Fast charging allows the PED to draw current between 0.5 and one ampere. Otherwise, the PED can draw current in the range of 0.15 ampere. As illustrated, the control network includes a set of electrical resistors. A first resistor (e.g., seventy-five kiloohms) is connected to the 5 VDC line on one end and to a second resistor (e.g., fifty-one kiloohms) and a pin of the USB connector. The second resistor is also connected to the 0 VDC line. Similarly, a third resistor (e.g., forty-three kiloohms) is connected to the 5 VDC line on one end and to a fourth resistor (e.g., fifty-one kiloohms) and another pin of the USB connector. The fourth resistor is also connected to the 0 VDC line.

Figure 7:
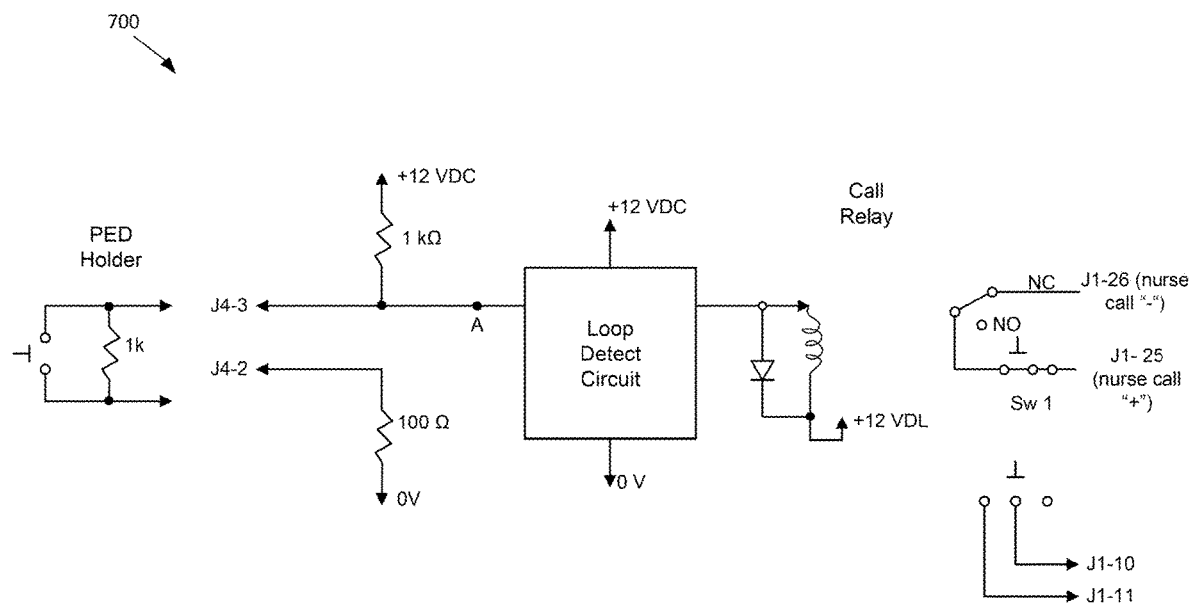
FIG. 7 illustrates a voltage converter between an input power connector and a USB connector, in accordance with embodiments of the present disclosure.

FIG. 7 illustrates a voltage converter 700 between an input power connector and a USB connector, in accordance with embodiments of the present disclosure. As illustrated, the voltage converter 700 is a 12 VDC to 5 VDC converter. Of course other configurations for the voltage converter 700 are possible depending on the available input power and the targeted output power. An input side of the voltage converter 700 is connected to the power input connector. An output side of the voltage converter 700 is connected to the USB connectors. In an example, a first pin and a second pin on the input side are connected to the 12 VDC line and the 0 VDC line, respectively. A third pin and a fourth pin on the output side are connected to a 5 VDC line and a 0 VDC line, respectively.

Figure 8:
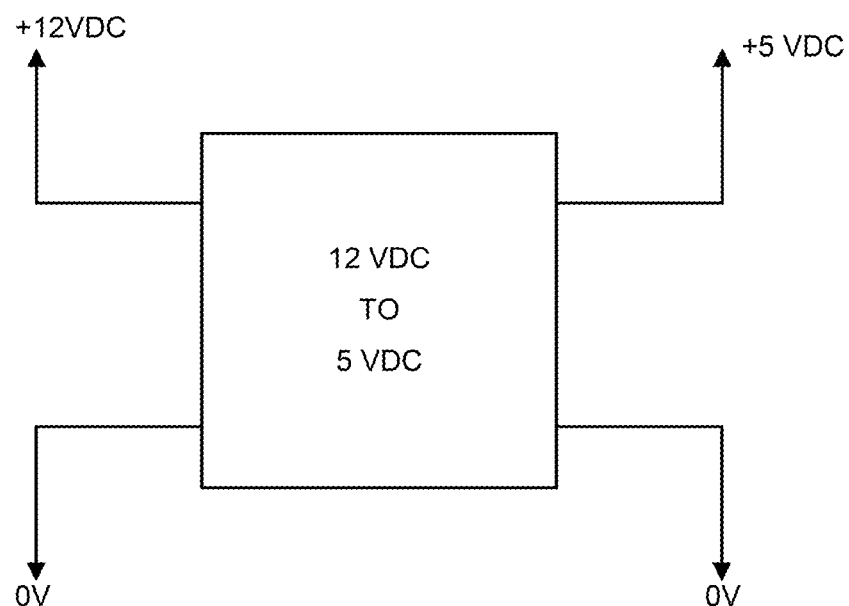
FIG. 8 illustrates an electrical voltage monitoring circuit, in accordance with embodiments of the present disclosure.

FIG. 8 illustrates an electrical voltage monitoring circuit 800, in accordance with embodiments of the present disclosure. In an example, the electrical voltage monitoring circuit 800 is installed between a PED input connector and a nurse call system connector (or, equivalently, a hospital bed connector). Here, the PED input connector and the nurse call system connector are examples of the PED connector 240 and the nurse call system connector 210 of FIG. 2. The electrical voltage monitoring circuit 800 includes an input side and an output side. The input side is connected to data pins of the PED connector and the output side is connected to data pins of the nurse call system connector. Accordingly, the electrical voltage monitoring circuit 800 couples data pins of the PED connector and data pins of the nurse call system connector. When a PED holder is coupled with the PED connector (e.g., by plugging a cable connected to the PED holder into the PED connector), an assistance request button is electrically coupled with the data pins of the PED connector and, accordingly, the input side of the electrical voltage monitoring circuit 800.

The electrical voltage monitoring circuit 800 outputs a voltage to the data pins of the nurse call system connector. This voltage indicates an operational mode from multiple operational modes of the data and power adapter. As explained herein above, the operational modes include an idle mode, a disconnected mode, and an assistance request mode. The value of the voltage depends on the connection with the assistance request button and whether an assistance request was initiated from this button. To support a supervised normally open mode as the idle mode, the electrical voltage monitoring circuit 800 can be configured to output an open circuit voltage and short circuit voltages on the output side depending on the voltage on the input side of the electrical voltage measuring circuit 800 (e.g., input voltage). The open circuit voltage corresponds to an input voltage falling within a first range that is associated with the idle mode. The short circuit voltages correspond to input voltages falling within a second range or third range, where these two ranges are associated with the disconnected mode and the assistance request mode. In an example, the first range is between 5 VDC and 7 VDC, the second range is larger than 7 VDC (e.g., between 7 VDC and 12 VDC), and the third range is less than 5 VDC (e.g., between 0 VDC and 5 VDC).

If the input voltage is in the first range, the output voltage corresponds to an open circuit indicating that the assistance request button is connected, but not pressed. If the input voltage is in the second range, the output voltage corresponds to a short circuit indicating that the assistance request button is disconnected. If the input voltage is in the third range, the output voltage corresponds to another short circuit indicating that the assistance request button is connected and pressed.

In an example, an assistance request button is implemented as an electrical switch in parallel with an electrical resistor (e.g., a one kiloohm resistor). This circuit of the assistance request button can be coupled with two data pins of the PED connector (shown in FIG. 8 as pins J4-2 and J4-3, where "J4" represents this connector) that in turn are connected to the input side of the electrical voltage monitoring circuit 800. The output side of the electrical voltage monitoring circuit 800 is connected to at least two pins of the nurse call system connector (shown in FIG. 8 as pins J1-25 and J1-26, where "J1" represents this connector).

The J4-2 pin is connected to the 0 VDC line via a first electrical resistor (e.g., a hundred ohm resistor) of the electrical voltage monitoring circuit 800. The J4-3 pin is connected to the 12 VDC line via a second electrical resistor (e.g., a hundred kiloohm resistor) of the electrical voltage monitoring circuit 800. The second electrical resistor is also connected to an input side of a loop detect circuit. This loop detect circuit is connected to the 12 VDC and 0 VDC lines. An output side of the loop detect circuit is connected to a relay contact that can be implemented as an inductor in parallel with a Zener diode, both of which may also be connected to the 12 VDC line. In turn, the relay contact is coupled with the J1-25 and J1-26 pins of the nurse call system connector.

An open circuit typically exists between the J1-25 and J1-26 pins. If the voltage measured by the loop detection circuit on its input side is in the first range, the relay contact does not change the connection between the J1-25 and J1-26 pins. Hence, an open circuit between these two pins can be interpreted as the DPA being operated in the idle mode. In comparison, if the voltage measured by the loop detection circuit on its input side is in the second or third range, the relay contact changes the connection between the J1-25 and J1-26 pins to create a short circuit between these two pins. If the short circuit is steady (e.g., is created for a period of time longer than a predefined time threshold, such as five seconds), the steadiness of the short circuit can be interpreted as a cord disconnect. If the short circuit is momentary (e.g., is detected for a period of time shorter than the predefined time threshold), the momentariness of the short circuit can be interpreted as a call request.

As further illustrated in FIG. 8, a first electrical switch can be connected to the J1-25 and J1-26 pins. This electrical switch is an example of the first electrical switch 282 of FIG. 2 and can be operated to create an open circuit between these two pins when a short circuit exists. In this way, the electrical switch can disengage the two pins to prevent a cord out alarm.

In addition, a second electrical switch can be connected to other pins of the nurse call system connector (e.g., to the J1-10 and J1-11 pins of this connector). This electrical switch is an example of the second electrical switch 284 of FIG. 2 and can be operated to create a short circuit between these two pins when an open circuit exists (this open circuit corresponds to a bed being disconnected from the hospital bed connector of the DPA). In this way, the electrical switch can disengage the two pins to also prevent a cord out alarm.

Other configurations of the electrical voltage monitoring circuit 800 are possible. For example, a second relay contact can be connected to the loop detection circuit on its output side. In this configuration, the first relay contact can be used to short the J1-25 and J1-26 pins in case of an assistance call request. The second relay contact can be used to short the J1-10 and J1-11 pins in case of a disconnection of the PED holder.

In other variations, the hospital bed connector and the nurse call system connector can include pins dedicated for bed status data. The PED connector can include additional data pins connected to these dedicated pins. When coupled with a PED, the additional data pins are usable to provide the bed status data to the PED.

Figure 9:
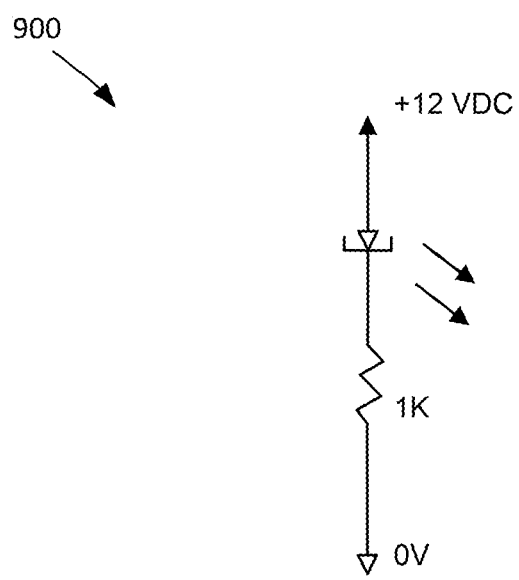
FIG. 9 illustrates connections to a light source, in accordance with embodiments of the present disclosure.

FIG. 9 illustrates connections to a light source 900, in accordance with embodiments of the present disclosure. In a first example, the light source 900 indicates whether power is available to a PED through a PED connector, similarly to the first light source 292 of FIG. 2. In this example, the light source 900 is implemented as a light emitting diode (LED)

connected on a first end to a first point on the 12 VDC line and on a second end to an electrical resistor (e.g., a one kiloohm resistor) that in turn is connected to the 0 VDC line. The first connection point can be along an electrical connection to a 12 VDC pin of a power input connector or to a 12 VDC pin of the PED connector.

In a second example, the light source 900 indicates whether a bed is disconnected (e.g., whether a bed connector is decoupled from the DPA), similarly to the second light source 294 of FIG. 2. In this example, the light source 900 is implemented as an LED electrically coupled on a first end to a pin of a hospital bed connector and on a second end to an electrical resistor (e.g., a one kiloohm resistor) that in turn is connected to the 0 VDC line.

In a third example, the light source 900 indicates whether an assistance request to a nurse call system can be initiated from an assistance request button of a PED, a PED holder, and/or a cable coupling the PED holder or PED with the DPA, similarly to the third light source 296 of FIG. 2. In this example, the light source 900 is implemented as an LED connected on a first end to an output side of a loop detection circuit of an electrical voltage measurement circuit, similar to the circuit 800 of FIG. 8, and on a second end to an electrical resistor (e.g., a one kiloohm resistor) that in turn is connected to a second point on the 0 VDC line. In addition, the light source can include hardware and/or software logic (e.g., a microprocessor, a field-programmable gate array, and/or another electric circuit) to change an emission property of the LED based on the operational state of the DPA. For instance, if the voltage across the light source 900 falls within a first range corresponding to the idle mode, the emission property is set to a particular configuration (e.g., a green light is emitted). If the voltage across the light source 900 falls within a second range or a third range corresponding to the disconnected mode and assistance request mode, respectively, the emission property is changed to the relevant configuration (e.g., a red light is emitted for the disconnected mode and a blue light is emitted for the assistance request mode).

Figure 10:
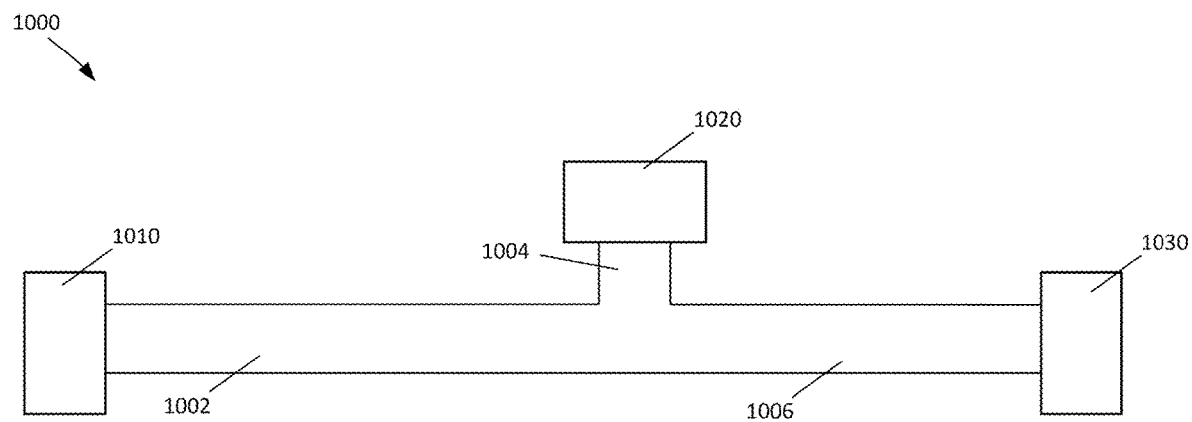
FIG. 10 illustrates a power and data cable that can be connected to a data and power adapter and a PED, in accordance with embodiments of the present disclosure.

FIG. 10 illustrates a power and data cable 1000 that can be connected to a data and power adapter and a PED, such as the DPA 150 and the PED 122, in accordance with embodiments of the present disclosure. In an example, the power and data cable 1000 is a single cable that carries power and data. In this example, the single cable can include a first set of wires for carrying power and a separate, second set of wires for carrying data. Alternatively, the single cable can include a set of wires that carries both power and data. In this example, a same wire can be used simultaneously for power and data. In this example also, only a subset of the wires can be simultaneously for power and data, whereas a remaining subset of the wires can be dedicated to power or data. In an illustration, the single cable is a POE cable, where the power and data is carried according to a POE protocol.

In the illustration of FIG. 3, the power and data cable 1000 includes a first portion 1002, a second portion 1004, a third portion 1006, a first connector 1010, a second connector 1020, and a third connector 1040. Each of the portions 1002-1006 includes one or more sets of wires, as discussed above, and mates with one of the connectors 1010-1030. In particular, the wires of the first portion 1002 are mated with and end at the first connector 1010. The second portion 1004 branches off from the first portion 1002 and/or the third portion 1006, and the wires of the second portion 1004 are mated with and end at the second connector 1020. The third portion 1006 is opposite to the first portion 1002 and the wires of the third portion 1006 are mated with and end at the third connector 1030.

The first connector 1010 can be a plug connector and/or a female receptacle that can be connected with a bed system or a bed connector. Power and/or data, including an assistance request signal, can be supplied to and/or received from the bed system via the first connector 1010. For instance, the first connector 1010 is a thirty-seven pins connector. The second connector 1020 can be a plug connector and/or a female receptacle that can be connected with the PED or a PED holder that holds the PED. Power and/or data can be supplied to and/or received from the PED via the second connector 1020. For instance, the second connector 1020 is a USB connector or a lightning connector. The third connector 1030 can be a plug connector and/or a female receptacle that can be connected with the power and data adapter. Power and/or data, including an assistance request signal, can be supplied to and/or received from the power and adapter via the third connector 1030. For instance, the third connector 1030 is a thirty-seven pins connector. Other variations to the connectors 1010-1030 are possible. For instance, any of the connectors 1010-1030 can be an electrical connector, a magnetic connector, and/or a fiber connector that that can be coupled, via one or more wired connections, with the relevant client (e.g., bed system, bed connector, PED, PED holder, and power and data adapter as applicable). Additionally or alternatively, any of the connectors 1010-1030 an be a radio frequency connector and/or an optical connector (e.g., a network interface) that can be coupled, via one or more wireless connections, with the relevant client.

The power and data cable 1000 can include additional components. For instance, one or more assistance request buttons can be included in one or more of the portions 1002-1006. In addition, the power and data cable 1000 can include one or magnetic connectors within any of the portions 1002-1006. A magnetic connector included in the power and data cable 1000 can couple the connectors 1010-1030.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A data and power adapter comprising:
a housing;
a first connector comprising first connections configured to connect the data and power adapter with a nurse call system of a hospital;
a second connector configured to connect the data and power adapter with a personal electronic device (PED) holder via a cable connected to the second connector, the second connector comprising a first set of connections configured to provide power, the second connector further comprising a second set of connections configured to receive a request signal corresponding to a request button and/or corresponding to a nurse call system control of a location that includes the data and power adapter, the second connector or the cable comprising a disconnectable component, wherein the PED holder includes the request button, and wherein the PED holder is connected to a first PED;
a third connector configured to connect the data and power adapter with a patient bed system of the hospital, the third connector comprising third connections;
a fourth connector configured to provide power to a second PED that is different from the first PED;
an indicator configured to indicate a first disconnect to the nurse call system when the PED holder disconnects; and
the indicator configured to indicate a second disconnect to the nurse call system when the patient bed system disconnects;
wherein a subset of the first connections of the first connector and the second set of connections of the second connector are electrically connected, and
wherein a subset of the third connections of the third connector is electrically connected with at least one of the first connections or the second set of connections.

2. The data and power adapter of claim 1, wherein each of the second connector and the fourth connector has a smaller number of pins than the first connector, and wherein each of the first connector and the third connector comprises thirty-seven pins, and further comprising:
a first set of electrical wires that connects at least one of the first connections of the first connector or the third connections of the third connector with the second set of connections of the second connector; and
a second set of electrical wires that connects the first connections of the first connector with the third connections of the third connector.

3. The data and power adapter of claim 2, further comprising:
a fifth connector in the housing, the fifth connector comprising fourth connections to a power source of the hospital; and
a third set of electrical wires that connects the fourth connections of the fifth connector with the first set of connections of the second connector.

4. The data and power adapter of claim 3, further comprising at least one of:
a rechargeable power source electrically coupled with the second connector and the fifth connector; or
a network interface card electrically coupled with the second connector.

5. The data and power adapter of claim 1, further comprising:
a power converter electrically coupled with the first set of connections of the second connector, wherein the fourth connector comprises a universal serial bus (USB) connector in the housing, the USB connector electrically coupled with the power converter.

6. The data and power adapter of claim 1, further comprising:
an electrical voltage monitoring circuit that electrically couples the first connections of the first connector and the second set of connections of the second connector.

7. The data and power adapter of claim 6, wherein the electrical voltage monitoring circuit outputs a voltage to the first connections of the first connector, wherein the voltage indicates an operational mode from multiple operational modes of the data and power adapter.

8. The data and power adapter of claim 7, wherein the voltage being in a first range indicates that the operational mode is an idle mode, wherein the voltage being in a second range indicates that the operational mode is a disconnected mode, and wherein the voltage being in a third range indicates that the operational mode is an assistance request mode.

9. The data and power adapter of claim 8, wherein the first range is between 5 VDC and 7 VDC, wherein the second range is larger than 7 VDC, and wherein the third range is less than 5 VDC.

10. The data and power adapter of claim 8, wherein the idle mode indicates that the request button is electrically coupled to the second connector and that no request signal exists on the second set of connections of the second connector, wherein the disconnected mode indicates that the request button is electrically disconnected from the second connector, and wherein the assistance request mode indicates that the request signal exists on the second set of connections of the second connector.

11. The data and power adapter of claim 8, wherein the second set of connections of the second connector are electrically coupled with a first pin and second pin of the first connector, wherein the electrical voltage monitoring circuit comprises an electrical relay that connects the first pin and the second pin to create a short circuit in response to the voltage being in the second range or the third range.

12. The data and power adapter of claim 11, further comprising:
- a first electrical switch in the housing between the first pin and the second pin; and
- a second electrical switch in the housing between two other pins of the first connector.

13. The data and power adapter of claim 8, wherein the second set of connections of the second connector are electrically coupled with a first pin and second pin of the first connector, wherein the electrical voltage monitoring circuit comprises a first electrical relay that connects the first pin and the second pin to create a first short circuit in response to the voltage being in the third range, and wherein the electrical voltage monitoring circuit further comprises a second electrical relay that connects two other pins of the first connector to create a second short circuit in response to the voltage being in the second range.

14. The data and power adapter of claim 7, wherein the indicator comprises a light source in the housing, wherein the light source is electrically coupled with the second connector, wherein an emission property of the light source varies between the multiple operational modes of the data and power adapter, and wherein the emission property of the light source comprises at least one of a wavelength of emitted light, an intensity of the emitted light, or an emission pattern of the emitted light.

15. The data and power adapter of claim 1, wherein the third connector is configured to connect the data and power adapter wirelessly or optically with the patient bed system.

16. The data and power adapter of claim 1, wherein the data and power adapter is wall mounted.

17. A system for hospital assistance calls, the system comprising:
- a data and power adapter that comprises:
  - a housing;
  - a first set of connectors disposed in the housing, the first set of connectors configured to connect the data and power adapter with a nurse call system of a hospital and with a patient bed system of the hospital, the first set of connectors comprising a first connector configured to connect the data and power adapter to the nurse call system, the first set of connectors further comprising a second connector configured to connect the data and power adapter to the patient bed system, wherein the first connector and the second connector are electrically connected and have a same pin out;
- a power and data cable comprising a second set of connectors, the second set of connectors configured to connect the power and data cable with the data and power adapter via a third connector, with the patient bed system, and with a personal electronic device (PED) holder via a cable connected to the third connector, wherein the third connector has a smaller number of pins than the first connector, wherein the PED holder includes a request button, and wherein the PED holder is connected to a first PED;
- a fourth connector configured to provide power to a second PED that is different from the first PED; and
- an indicator configured to indicate a first disconnect to the nurse call system when the PED holder disconnects; and
- the indicator configured to indicate a second disconnect to the nurse call system when the patient bed system disconnects.

18. The system of claim 17, wherein the fourth connector comprises a universal serial bus connector, a magnetic connector, or a lightning connector configured to connect the power and data cable with the second PED.

19. The system of claim 18, wherein the power and data cable comprises a plurality of branches, and wherein the universal serial bus connector, the magnetic connector, or the lightning connector mates with a branch of the plurality of branches of the power and data cable.

20. The system of claim 17, wherein the power and data adapter comprises a proximity sensor.

21. The system of claim 17, wherein the power and data adapter comprise an illumination source.

22. The system of claim 17, wherein an assistance request button is included in the power and data cable or the PED holder.

* * * * *